(12) United States Patent
Singer et al.

(10) Patent No.: US 6,531,509 B2
(45) Date of Patent: Mar. 11, 2003

(54) STABLE GABAPENTIN CONTAINING MORE THAN 20 PPM OF CHLORINE ION

(75) Inventors: Claude Singer, Kfar Saba (IL); Gideon Pilarski, Holon (IL); Michael Pesachovich, Givat Shmuel (IL); Edward Schwartz, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/880,854

(22) Filed: Jun. 15, 2001

(65) Prior Publication Data

US 2002/0061931 A1 May 23, 2002

Related U.S. Application Data

(60) Provisional application No. 60/211,967, filed on Jun. 16, 2000.

(51) Int. Cl.⁷ .............................................. A61K 31/195
(52) U.S. Cl. ........................ 514/561; 562/504; 562/507
(58) Field of Search ........................................ 514/561

(56) References Cited

U.S. PATENT DOCUMENTS

| | | | |
|---|---|---|---|
| 4,024,175 A | 5/1977 | Satzinger et al. | 260/468 |
| 4,087,544 A | 5/1978 | Satzinger et al. | 424/305 |
| 4,152,326 A | 5/1979 | Hartenstein et al. | 546/16 |
| 4,894,476 A | 1/1990 | Butler et al. | 562/504 |
| 4,960,931 A | 10/1990 | Butler et al. | 562/507 |
| 5,025,035 A | 6/1991 | Wallace | 514/530 |
| 5,068,413 A | 11/1991 | Steiner et al. | 562/507 |
| 5,084,479 A | 1/1992 | Woodruff | 514/53 |
| 5,091,567 A | 2/1992 | Geibel et al. | 562/507 |
| 5,132,451 A | 7/1992 | Jennings et al. | 562/507 |
| 5,319,135 A | 6/1994 | Jennings et al. | 562/507 |
| 5,362,883 A | 11/1994 | Jennings et al. | 548/408 |
| 5,693,845 A | 12/1997 | Jennings et al. | 558/431 |
| 6,054,482 A * | 4/2000 | Augart et al. | 514/561 |

FOREIGN PATENT DOCUMENTS

| WO | WO 00/07568 | 2/2000 |
|---|---|---|
| WO | WO 01/13894 A1 | 1/2001 |

\* cited by examiner

*Primary Examiner*—Dwayne C. Jones
(74) *Attorney, Agent, or Firm*—Kenyon & Kenyon

(57) ABSTRACT

Pharmaceutical compositions containing substantially pure and stable gabapentin are disclosed wherein gabapentin contains an anion of a mineral acid, such as chloride, in amounts greater than 20 ppm.

7 Claims, No Drawings

STABLE GABAPENTIN CONTAINING MORE THAN 20 PPM OF CHLORINE ION

CROSS-REFERENCE TO RELATED APPLICATIONS

This invention relates to PCT Application No. WO98/28255, filed Jul. 2, 1998, also assigned to the assignee of the present invention and incorporated herein by reference; this invention also claims priority to U.S. Provisional Application No. 60/211,967 filed Jun. 16, 2000.

FIELD OF THE INVENTION

The present invention relates to a pharmaceutical composition containing therapeutically effective amount of gabapentin and its derivatives in combination with effective carriers. More particularly, the present invention relates to a composition and a process for manufacturing pure and stable gabapentin having greater than 20 ppm of chloride ion.

BACKGROUND OF THE INVENTION

Gabapentin is 1-(aminomethyl)-1-cyclohexaneacetic acid, having the chemical structure of formula I:

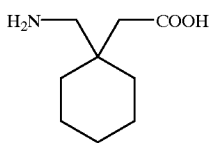

(I)

Gabapentin is used for treating cerebral diseases such as epilepsy, faintness attacks, hypokinesis and cranial traumas. U.S. Pat. No. 4,024,175 to Satzinger et al., incorporated herein by reference, discloses that gabapentin of formula (I) shows hypothermal and, in some cases, narcosis-potentiating or sedating properties as well as protective effect against cardiozole cramp in animals. Finally, gabapentin has been found especially useful in treating geriatric patients. As such, there has been a need for producing pure and stable gabapentin.

U.S. Pat. No. 6,054,482 to Augart et al. discloses that preparation and long-term storage of gabapentin presents several problems since (i) during the preparation the compounds shows considerable variations without apparent reason, and (ii) the long-term storage of even very pure gabapentin showed differing stabilities with progressively long storage times. Augart further discloses that the toxic lactam compound of formula (II)

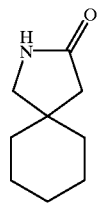

(II)

forms during the preparation and storage of gabapentin. According to Augart, because the lactam has a higher toxicity than gabapentin, its presence in gabapentin should be limited if not eliminated. To combat lactam formation and provide product stability, Augart stresses the importance of (i) starting with gabapentin raw material that contains 0.5% or less of corresponding lactam, (ii) not allowing the anion of a mineral acid in the composition to exceed 20 ppm, and (iii) using a specifically selected adjuvant that is not adverse to gabapentin stability.

According to Augart, the following adjuvants (or excipients) had no noticeable influence on the stability of gabapentin, and as such, they were taught to be acceptable adjuvants for use with gabapentin: hydroxypropylmethylcellulose, polyvinylpyrrolidone, crospovidon, poloxamer 407, poloxamer 188, sodium starch glycolate, copolyvidone, maize starch, cyclodextrin, lactose, talc, as well as co-polymers of dimethylamino-methacrylic acid and neutral methacrylic acid ester.

Conversely, Augart discloses that the following adjuvants reduce the stability of gabapentin and should be avoided: modified maize starch, sodium croscarmelose, glycerol behenic acid ester, methacrylic acid co-polymers (types A and C), anion exchangers titanium dioxide and silica gels such as Aerosil 200.

The composition and method disclosed in Augart are industrially impractical and technically unnecessary. It has now been found that Augart's reliance on maintaining the anion of a mineral acid as not exceeding 20 ppm is misplaced. Thus, gabapentin and pharmaceutical formulations of gabapentin can be prepared and stored such that initially they do not contain more than 0.5% of the lactam, and even after one year of storage at 25° C. and 60% atmospheric humidity, the conversion of gabapentin to its corresponding lactam does not exceed 0.2% by weight of gabapentin. That is, gabapentin and pharmaceutical formulations of gabapentin have been found to be stable even though such formulations do not meet Augart's requirements (ii) and (iii).

The specific mineral acid disclosed by Augert is hydrochloric acid (column 3, lines 61–63; column 5, lines 24–29; exampes 1 and 2). The specification states, in particular The active materials of formula (I) [including gabapentin] must be prepared as highly purified, nonderivatized free amino acids, for example, from the corresponding hydrochloride by ion exchange. The proportion of remaining hydrochloride admixtures should thereby not exceed 20 ppm.

(Column 5, lines 24–29).

20 ppm of gabapentin hydrochloride corresponds to roughly 3 ppm of chloride ion, due to the higher molecular weight of gabapentin.

Augert's claims require gabapentin with "less than 20 ppm of the anion of a mineral acid", e.g. chloride.

SUMMARY OF THE INVENTION

Accordingly, the present invention relates to a pharmaceutical composition containing a pharmaceutically effective amount of gabapentin containing more than 20 ppm of an anion of a mineral acid and which initially contains less than 0.5% of a corresponding lactam and after one year of storage at 25° C. and 60% atmospheric humidity the conversion of gabapentin to its corresponding lactam does not exceed 0.2% by weight of gabapentin.

The present invention also relates to a process for preparing a stable pharmaceutical formulation containing gabapentin with more than 20 ppm of the anion of a mineral acid and which initially contains less than 0.5% of a corresponding lactam and after storage for one year at 55° C. and 60% atmospheric humidity the conversion of gabapentin to its corresponding lactam does not exceed 0.2% by weight of gabapentin.

DETAILED DESCRIPTION OF THE PREFERRED EMBODIMENTS

The subject invention will now be described in greater detail for preferred embodiments of the invention, it being understood that these embodiments are intended only as illustrative examples and the invention is not to be limited thereto.

As will be illustrated through exemplary embodiments 1–16, gabapentin may be prepared from the hydrochloride salt of gabapentin (gabapentin hydrochloride) and that in purified form gabapentin may contain more than 20 ppm of chloride ion in the composition as measured by the amount of chloride ion in the composition.

Exemplary embodiments 17–19 illustrate formulations of gabapentin containing varying amounts of chloride ion, some of which are greater than 20 ppm and some less, and all of which initially contain less than 0.5% of lactam and after one year of storage at 25° C. and 60% humidity, the conversion of gabapentin to its corresponding lactam is measured not to exceed 0.2% by weight of gabapentin.

Commonly known adjuvants (also referred to as excipients) which can be utilized in a gabapentin formulation of the present invention may include for example, modified maize starch, sodium croscarmelose, titanium dioxide, and silica gels such as Aerosil 200. Hydroxypropylmethylcellulose, polyvinylpyrrolidone, crospovidon, poloxamer 407, poloxamer 188, sodium starch glycolate, copolyvidone, maize starch, cyclodextrin, lactose, talc, co-polymers of dimethylamino-methacrylic acid and neutral methacrylic acid ester may also be used. The list of adjuvants is not an exhaustive list and it would be within the scope of the claimed invention to use any known adjuvant that would behave similar to those enumerated herein.

Certain specific representative embodiments of the invention are described in detail below, the materials, apparatus and process steps being understood as examples that are intended for illustrative purposes only. Consequently, it will be noted that the invention is not intended to be limited to the methods, materials, conditions, precess parameters, apparatus and the like specifically recited herein.

In the examples below chloride ion concentration is measured by any commonly known method, such as for example, by titration with $AgNO_3$, or pH electrode or chromatography.

EXAMPLE 1

The following raw material were used:

| | |
|---|---|
| Gabapentin hydrochloride | 18.2 g |
| Isopropanol for dissolution | 160 ml |
| Active carbon SX1 | 1.1 g |
| Ethylacetate | 268 ml |
| Tributylamine | 19.5 g |
| Methanol for washing | 23 ml |

A) Preparation of Crude gabapentin

Gabapentin hydrochloride was dissolved in 130 ml of dry isopropanol at 25° C. by mixing. Next, 1.1 grams of active carbon was added and the suspension was heated to 40° C. and maintained at this temperature for 2 hours. The suspension was then filtered at 40° C. and the filter cake was washed twice with additional 15 ml of isopropanol each time. The washings were added to the already separated solution of gabapentin hydrochloride in isopropanol. The solution was concentrated to dryness in vacuum (Approximately 10 mm Hg) to a constant weight. The temperature of the heating bath was maintained (maximally) at 35° C. during this operation. Thereafter, 245 ml of ethylacetate was added to the dry residue of gabapentin hydrochloride and the solution was mixed. After half an hour of mixing at 25° C., an amount of 19.5 grams of tributylamine was added during the subsequent 30 minutes. The mixing continued for an additional two hours at the same temperature.

The gabapentin base which was formed during this operation was separated from the suspension through filtration. The filter cake was washed with 23 ml of ethylacetate and 23 ml of methanol to give crude gabapentin.

B) Gabapentin Purification

The following raw material were used:

| | |
|---|---|
| Methanol for suspending | 52.5 ml |
| Methanol for washing | 2 × 15 ml |

Wet crude gabapentin prepared according to Step A was suspended in 52.5 ml of methanol for 14 hours at approximately 25° C. and stirred. Thereafter, the solid gabapentin was separated from the suspension by filtration. The filter cake was washed twice with 15 ml of methanol and than dried under vacuum giving pure gabapentin. The yield was 72%.

The following data regarding the chlorine anion content of the above-prepared gabapentin were obtained:

TABLE 1

Anion content and pH values after the reslurry in methanol

| Run | Cl (ppm) | pH |
|---|---|---|
| A | 4 | 6.94 |
| B | 20 | 7.01 |
| C | <5 | 7.04 |
| D | 40 | 6.97 |
| E | 35 | 6.92 |
| F | 15 | 6.84 |

Gabapentin purified according to these procedures contains less than 0.5% lactam as measured by HPLC vs. standard. After a year of storage at 25° C. and 60% relative humidity, the conversion of gabapentin to its corresponding lactam does not exceed 0.2% by weight of gabapentin.

For a better control of the pH of pure gabapentin several basic agents were added. Some examples of added basic agents are given in the following Examples.

EXAMPLE 2

The following raw material were used:

| | |
|---|---|
| Methanol for suspending | 52.5 ml |
| Methanol for washings | 2 × 15 ml |
| Tributylamine | ~0.3 equivalents |

The wet crude gabapentin (as in Step 1A) was suspended in 52.5 ml of methanol for 14 hours and at 25° C. and stirred. Tributylamine was added to the suspension. After 14 hours of stirring the solid gabapentin was separated from the suspension by filtration. The filter cake was then washed twice, each time with 15 ml of methanol and than dried under vacuum resulting in pure gabapentin with a yield of 87%, pH of 7.15 and chlorine anion content of 50 ppm.

Gabapentin so prepared contains less than 0.5% by weight of lactam, and, after a year of storage at 25° C. and 60% relative humidity the conversion of gabapentin to its corresponding lactam is found not to exceed 0.2% by weight of gabapentin.

EXAMPLE 3

The following raw material were used:

| Methanol for suspending | 52.5 ml |
| --- | --- |
| Methanol for washing | 2 × 15 ml |
| Sodium methoxide | ~0.001 equivalents |

The wet crude gabapentin (as in Example 1, step A) was suspended in 52.5 ml of methanol for 14 hours and kept at 25° C. Sodium methoxide was added to the suspension. After 14 hours of stirring, the solid gabapentin was separated from the suspension by filtration. The filter cake was then washed twice with 15 ml of methanol, then dried under vacuum, resulting in pure gabapentin having a yield of 85%, pH of 6.8, and chlorine anion content of 50 ppm. Gabapentin so prepared contained less than 0.5% by weight of lactam, and, after a year of storage at 25° C. and 60% relative humidity, the conversion of gabapentin to its corresponding lactam is found not to exceed 0.2% by weight of gabapentin.

It should be noted that the solvents and the base used in Example 1A were not unique. In addition, it should be noted that in Examples 4–9 gabapentin pure was always prepared as in Example 1B and the results (Cl$^-$ content and yield) refer to gabapentin pure.

EXAMPLE 4

The following raw material were used:

| Gabapentin hydrochloride (100%) | 18.2 g |
| --- | --- |
| Isopropanol for dissolution | 160 ml |
| Active carbon SX1 | 1.1 g |
| Tributylamine | 19.5 g |
| Methanol for washing | 23 ml |

In this Example, gabapentin hydrochloride was dissolved in 130 ml of dry isopropanol at 25° C. Then 1.1 grams of active carbon was added and the suspension was heated to 40° C. and maintained at this temperature for 2 hours. The suspension was filtered at 40° C. and the filter cake was then washed twice, each time with an additional 15 ml of isopropanol. The washings were added to the already separated solution of gabapentin hydrochloride in isopropanol. After half an hour of mixing at 25° C., 19.5 grams of tributylamine was added during half an hour and the mixing was continued for two hours at the same temperature. The formed gabapentin base was separated from the suspension by filtration and washed with 23 ml of methanol to give gabapentin crude. After reslurry as in Example 1B gabapentin pure was obtained at a yield of 58.8% and chloride anion content of 7 ppm Cl$^-$.

Gabapentin so prepared contained less than 0.5% by weight of lactam, and, after a year of storage at 25° C. and 60% relative humidity, the conversion of gabapentin to its corresponding lactam is found not to exceed 0.2% by weight of gabapentin.

EXAMPLE 5

The following raw material were used:

| Gabapentin hydrochloride (100%) | 18.2 g |
| --- | --- |
| Isopropanol for dissolution | 160 ml |
| Active carbon SX1 | 1.1 g |
| Ethylacetate | 268 ml |
| Trihexylamine | 28.3 g |
| Methanol for washing | 23 ml |

Gabapentin hydrochloride was dissolved in 130 ml dry isopropanol at 25° C. by mixing, then 1.1 g of active carbon was added and the suspension was heated to 40° C. and maintained for two hours at 40° C. The suspension was filtered at 40° C. and the filter cake was washed twice with additional 15 ml of isopropanol each time. The washings were added to the already separated solution of gabapentin hydrochloride in isopropanol. The solution was concentrated to dryness in vacuum (approximately 10 mm Hg) to constant weight. The temperature of the heating bath was maintained at maximum 35° C. during this operation. Next, 245 ml of ethylacetate was added to the dry residue of gabapentin hydrochloride and the mixing was started. After half an hour of mixing at 25° C., an amount of 28.3 grams of trihexylamine was added during half an hour and the mixing was continued for an additional two hours at the same temperature. The formed gabapentin base was separated from the suspension by filtration. The filter cake was washed with 23 ml of ethylacetate and 23 ml of methanol to give gabapentin crude. After reslurry as in Example 1B, gabapentin pure was obtained having a yield of 75.0% and chloride anion content of 213 ppm.

EXAMPLE 6

The following raw material were used:

| Gabapentin hydrochloride (100%) | 18.2 g |
| --- | --- |
| Isopropanol for dissolution | 160 ml |
| Active carbon SX1 | 1.1 g |
| Ethylacetate | 268 ml |
| Tripropylamine | 15 g |
| Methanol for washing | 23 ml |

Gabapentin hydrochloride was dissolved in 130 ml dry isopropanol at 25° C. by mixing, then 1.1 g of active carbon was added and the suspension was heated to 40° C. and maintained during two hours at 40° C. The suspension was filtered at 40° C. and the filter cake was washed twice with additional 15 ml of isopropanol each time. The washings were added to the already separated solution of gabapentin hydrochloride in isopropanol. The solution was concentrated to dryness in vacuum (~10 mm Hg) to constant weight. The temperature of the heating bath was maintained at maximum 35° C. during this operation. Next, 245 ml of ethylacetate was added to the dry residue of gabapentin hydrochloride and mixing commenced. After half an hour of mixing at 25° C., fifteen grams of tripropylamine was added during half an hour and the mixing was continued for two hours at the same temperature. The formed gabapentin base was separated from the suspension by filtration. The filter cake was washed with 23 ml of ethylacetate and 23 ml of methanol to give gabapentin crude. After a reslurry process, as in Example 1B, gabapentin pure was obtained having a yield of 68.0% and chloride anion content of 142 ppm.

EXAMPLE 7

The following raw material were used:

| | |
|---|---|
| Gabapentin hydrochloride (100%) | 18.2 g |
| Isopropanol for dissolution | 160 ml |
| Active carbon SX1 | 1.1 g |
| Acetonitrile | 268 ml |
| Tributylamine | 19.5 g |
| Methanol for washing | 23 ml |

Gabapentin hydrochloride was dissolved in 130 ml of dry isopropanol at 25° C. by mixing, then 1.1 g of active carbon was added and the suspension was heated to 40° C. and maintained for two hours at 40° C. The suspension was filtered at 40° C. and the filter cake was washed twice with additional 15 ml of isopropanol. The washings were added to the already separated solution of gabapentin hydrochloride in isopropanol. The solution was concentrated to dryness in vacuum (~10 mm Hg) to constant weight. The temperature of the heating bath was maintained at a maximum temperature of 35° C. during this operation. Next, 245 ml of acetonitrile was added to the dry residue of gabapentin hydrochloride and mixing commenced. After half an hour of mixing at 250° C., an amount of 19.5 g of tributylamine was added during 30 minutes and the mixing was continued for two hours at the same temperature. The formed gabapentin base was separated from the suspension by filtration. The filter cake was washed with 23 ml of acetonitrile and 23 ml of methanol to give gabapentin crude. After reslurry as in Example 1B, gabapentin pure was obtained having a yield of 67.8%, and anion content of 142 ppm.

EXAMPLE 8

The following raw material were used:

| | |
|---|---|
| Gabapentin hydrochloride (100%) | 18.2 g |
| Isopropanol for dissolution | 160 ml |
| Active carbon SX1 | 1.1 g |
| Dimethylcarbonate | 268 ml |
| Tributylamine | 19.5 g |
| Methanol for washing | 23 ml |

Gabapentin hydrochloride was dissolved in 130 ml of dry isopropanol at 25° C. by mixing, then 1.1 g of active carbon was added and the suspension was heated to 40° C. and maintained at 40° C. for two hours. The suspension was filtered at 40° C. and the filter cake was washed twice with additional 15 ml of isopropanol. The washings were added to the already separated solution of gabapentin hydrochloride in isopropanol. The solution was concentrated to dryness in vacuum (~10 mm Hg) to constant weight. The temperature of the heating bath was maintained at maximum of 35° C. during this operation. Next, 245 ml of dimethylcarbonate was added to the dry residue of gabapentin hydrochloride and the mixing was started. After half an hour of mixing at 25° C., an amount of 19.5 g of tributylamine was added during half an hour and the mixing was continued for two hours at the same temperature. The formed gabapentin base was separated from the suspension by filtration. The filter cake was washed with 23 ml of dimethylcarbonate and 23 ml of methanol to give gabapentin crude. After reslurry as in Example 1B, gabapentin pure was obtained, having a yield of 57.9%, and anion content of 142 ppm.

EXAMPLE 9

The following raw material were used:

| | |
|---|---|
| Gabapentin hydrochloride (100%) | 18.2 g |
| Isopropanol for dissolution | 160 ml |
| Active carbon SX1 | 1.1 g |
| Isopropylacetate | 268 ml |
| Tributylamine | 19.5 g |
| Methanol for washing | 23 ml |

Gabapentin hydrochloride is dissolved in 130 ml of dry isopropanol at 25° C. by mixing, then 1.1 g of active carbon was added and the suspension was heated to 40° C. and maintained for two hours at 40° C. The suspension was filtered at 40° C. and the filter cake was washed twice with additional 15 ml of isopropanol each time. The washings were added to the already separated solution of gabapentin hydrochloride in isopropanol. The solution was concentrated to dryness in vacuum (~10 mm Hg) to constant weight. The temperature of the heating bath was maintained at maximum 35° C. during this operation. Next, 245 ml of isopropylacetate was added to the dry residue of gabapentin hydrochloride and mixing commenced. After half an hour of mixing at 25° C., an amount of 19.5 g of tributylamine was added during half an hour and the mixing was continued for two hours at the same temperature. The formed gabapentin base was separated from the suspension by filtration. The filter cake was washed with 23 ml of isopropylacetate and 23 ml of methanol to give gabapentin crude. After reslurry as in Example 1B, gabapentin pure was obtained having a yield of 57.9% and an anion content of 142 ppm.

EXAMPLE 10

(The neutralization reaction as in Example 1, however, the reslurry in methanol is replaced by a crystallization in methanol.)

The following raw material were used:

| | |
|---|---|
| Methanol for dissolution | 180 ml |
| Methanol for washing | 2 × 12 ml |

The gabapentin crude (Step 1A) was suspended in 180 ml of methanol at 25° C. The suspension was heated while mixing to 55° C. when gabapentin was dissolved. The solution was then cooled slowly for an hour to 25° C. At 25° C. the solution was concentrated to a volume of 50 ml. The suspension was stirred for twelve hours at 25° C. After 12 hours, the solid gabapentin was separated from the suspension by filtration. The filter cake was washed twice with 12 ml of methanol then dried under vacuum to give gabapentin pure (yield: 72%). Following Cl⁻ contents of gabapentin and pH values were obtained and tabulated in TABLE 2 as follows:

TABLE 2

| Anion content and PH values for crystallization in methanol | | |
|---|---|---|
| Run | Cl (ppm) | pH |
| A | 4 | 6.94 |
| B | <5 | 72 |
| C | 150–200 | 6.9 |

For a better control of the pH of gabapentin pure several basic agents were added. Some examples of added basic agents are given in the following examples

EXAMPLE 11

The following raw material were used:

| | |
|---|---|
| Methanol for suspending | 52.5 ml |
| Methanol for washings | 2 × 15 ml |
| Tributylamine | ~0.34 equivalents |

The gabapentin crude was suspended in 180 ml of methanol at 25° C. The suspension was then heated, while mixing, to 55° C. when gabapentin was dissolved. Tributylamine was added to the solution and the solution was cooled slowly during an hour to a temperature of 25° C. At 25° C. the solution was concentrated to a volume of 50 ml. The suspension was stirred for twelve hours at 25° C. After 12 hours the solid gabapentin was separated from the suspension by filtration. The filter cake was washed twice with 12 ml of methanol and then dried under vacuum to give gabapentin pure having a yield of 81.4%, pH of 7.25 and chlorine anion content of 35 ppm.

Gabapentin so prepared contained less than 0.5% by weight of lactam, and, after a year of storage at 25° C. and 60% relative humidity, the conversion of gabapentin to its corresponding lactam does not exceed 0.2% by weight of gabapentin.

EXAMPLE 12

The following material were used:

| | |
|---|---|
| Methanol for suspending | 52.5 ml |
| Methanol for washings | 2 × 15 ml |
| Sodium methoxide | ~0.001 equivalents |

Crude gabapentin was suspended in 180 ml of methanol at 25° C. The suspension was heated under mixing to 55° C. when gabapentin was dissolved. Sodium methoxide was added to the solution and the solution was cooled slowly during one hour to 25° C. At 25° C. the solution was concentrated to a volume of 50 ml. The suspension was stirred for twelve hours at 25° C. After 12 hours the solid gabapentin was separated from the suspension by filtration. The filter cake was washed twice with 12 ml of methanol, then dried under vacuum to give gabapentin pure at a yield of 81.4%, pH of 7.08 and anion content of Cl− 20 ppm.

Gabapentin so prepared contained less than 0.5% by weight of lactam, and, after a year of storage at 25° C. and 50% relative humidity, the amount of lactam remained less than 0.5% by weight. After one year of storage at 25° C. and 60% relative humidity, the conversion of gabapentin to its corresponding lactam is found not to exceed 0.2% by weight of gabapentin.

EXAMPLE 13

The following material were used:

| | |
|---|---|
| Methanol for suspending | 52.5 ml |
| Methanol for washings | 2 × 15 ml |
| Sodium bicarbonate | ~0.05 equivalents |

Crude gabapentin was suspended in 180 ml of methanol at 25° C. The suspension was heated under mixing to 55° C. when gabapentin was dissolved. Sodium bicarbonate was added to the solution and the solution was cooled slowly for one hour to 25° C. At 25° C. the solution was concentrated to a volume of 50 ml. The suspension was stirred for twelve hours at 25° C. After 12 hours the solid gabapentin was separated from the suspension by filtration. The filter cake was washed twice with 12 ml of methanol, then dried under vacuum to give gabapentin pure having a yield of 72.4%, pH of 7.28 and anion (Cl−) content of 20 ppm.

Gabapentin so prepared contained less than 0.5% by weight of lactam, and, after a year of storage at 55° C. and 50% relative humidity, the amount of lactam remained less than 0.5% by weight. After a year of storage at 25° C. and 60% relative humidity, the conversion of gabapentin to its corresponding lactam is found not to exceed 0.2% by weight of gabapentin.

EXAMPLE 14

The following raw material were used:

| | |
|---|---|
| Methanol for suspending | 52.5 ml |
| Methanol for washing | 2 × 15 ml |
| Tetramethylammoniumhydroxide | ~0.002 equivalents |

Crude gabapentin was suspended in 180 ml of methanol at 25° C. The suspension was heated under mixing to 55° C. when gabapentin was dissolved. Tetramethylammoniumhydroxide was added to the solution and the solution was cooled slowly for one hour to 25° C. At 25° C. the solution was concentrated to a volume of 50 ml. The suspension was stirred for 12 hours at 25° C. After 12 hours the solid gabapentin was separated from the suspension by filtration. The filter cake was washed twice with 12 ml of methanol than dried under vacuum to give gabapentin pure having a yield of 75.8%, pH of 7.03 and anion content of (Cl−) 20 ppm.

Gabapentin so prepared contained less than 0.5% by weight of lactam.

EXAMPLE 15

The following raw material were used:

| | |
|---|---|
| Methanol for suspending | 52.5 ml |
| Methanol for washing | 2 × 15 ml |
| Tetrabutylammoniumhydroxide | ~0.002 equivalents |

Crude gabapentin was suspended in 180 ml of methanol at 25° C. The suspension was heated under mixing to 55° C. when gabapentin was dissolved. Tetrabutylammoniumhydroxide was added to the solution and the solution was cooled slowly during one hour to 25° C. At 25° C. the solution was concentrated to a volume of 50 ml. The suspension was stirred for 12 hours at 25° C. After 12 hours the solid gabapentin was separated from the suspension by filtration. The filter cake was washed twice with 12 ml of methanol, then dried under vacuum to give gabapentin pure having a yield of 77.6%, pH of 7.22 and anion (Cl−) content of 20 ppm.

EXAMPLE 16

The following raw material were used:

| | |
|---|---|
| Methanol for suspending | 52.5 ml |
| Methanol for washing | 2 × 15 ml |
| Sodiumtetraborate | ~0.05 equivalents |

Crude gabapentin was suspended in 180 ml of methanol at 25° C. The suspension was heated under mixing to 55° C. when gabapentin was dissolved. Sodiumtetraborate was added to the solution and the solution was cooled slowly for one hour to 25° C. At 25° C. the solution was concentrated to a volume of 50 ml. The suspension was stirred for 12 hours at 25° C. After 12 hours the solid gabapentin was separated from the suspension by filtration. The filter cake was washed twice with 12 ml of methanol and then dried under vacuum to give gabapentin pure having a yield of 75%, pH of 7.17 and anion content (Cl⁻) of 10 ppm.

EXAMPLE 17

The following gabapentin tablet formulation is prepared using gabapentin containing chloride ion ranging from 5 to 40 ppm and pH in the range of 6.84–7.04 according to Example 1. The following material is used:

| Ingredients | Amounts |
| --- | --- |
| gabapentin | 125 g |
| Corn Starch NF | 200 g |
| Cellulose, Microcrystalline | 46 g |
| Sterotex Powder HM | 4 g |
| Purified Water | q.s. or 300 ml |

Combine corn starch, cellulose, and gabapentin together in a mixer and mix for 2–4 minutes. Add water to this combination and mix for an addition 1–3 minutes. The resulting mix is spread on trays and dried in convection oven at 45–55° C. until a moisture level of 1 to 2% is obtained. The dried mix is then milled and added back to the mill mixture and the total is blended for additional 4–5 minutes. Compressed tables of 150 mg, 375 mg and 750 mg are formed using appropriate punches from the total mix.

The formulation is measured to contain less than 0.5% lactam and after one year of storage at 25° C. and 60% atmospheric humidity, the conversion of gabapentin to its corresponding lactam is found not to exceed 0.2% by weight of gabapentin.

EXAMPLE 18

Gabapentin of Example 2 (having chloride ion content of 50 ppm and pH of 7.15) is used to formulate tablets as in EXAMPLE 17, except that corn starch is replaced in each sample by one of the following adjuvants: pregelatinized starch, croscarmelose sodium, silica gel, titanium dioxide, talc, modified maize starch and maize starch.

The resulting gabapentin tablet of each sample is initially measured to have 0.5% by weight of a corresponding lactam, more than 50 ppm of chloride anion, and pH exceeding 6.8. The tablet is stored for one year at 25° C. and 60% atmospheric humidity and the increase in the lactam concentration is found not to exceed 0.2% by weight.

EXAMPLE 19

EXAMPLE 18 is repeated except that gabapentin of Example 4, having chloride ion of 7 ppm is used for formulating tablets. The resulting gabapentin tablet of each sample is initially measured to have 0.5% by weight of lactam and approximately 7 ppm of chloride anion. The tablet is stored for one year at 55° C. and 50% atmospheric humidity and the increase in the lactam concentration is found not to exceed 0.2% by weight.

Examples 17–19 show that, contrary to Augart's disclosure, the presence of anion of a mineral acid in an amount greater than 20 ppm does not adversely affect the stability of gabapentin when stored for one year at 25° C. and 60% humidity. The examples also show that the gabapentin formulations prepared in accordance with the invention showed adequate stability regardless of the type of adjuvant that were used.

We claim:

1. A pharmaceutical composition comprising gabapentin and initially containing less than 0.5% by weight of a corresponding lactam with respect to the weight of gabapentin and having greater than 20 ppm of an anion of a mineral acid with respect to the weight of gabapentin, which, after one year of storage at 25° C. and 60% humidity the conversion of gabapentin to its corresponding lactam does not exceed 0.2% by weight of gabapentin.

2. The pharmaceutical composition of claim 1 further comprising at least one adjuvant.

3. The pharmaceutical composition of claim 2, wherein at least one adjuvant is selected from the group consisting of modified maize starch, glycerol behenic acid ester, sodium croscarmelose, methacrylic acid co-polymers (types A and C), anion exchangers, titanium dioxide, silica gels hydroxypropylmethylcellulose, polyvinylpyrrolidone, crospovidon, sodium starch glycolate, copolyvidone, maize starch, cyclodextrin, lactose, talc, co-polymers of dimethylamino-methacrylic acid and neutral methacrylic acid ester.

4. The pharmaceutical composition of claim 1, wherein said anion of a mineral acid is a halide.

5. The pharmaceutical composition of claim 1, wherein the amount of said anion of a mineral acid does not exceed 100 ppm.

6. Gabapentin which contains less than 0.5% of a corresponding lactam with respect to the weight of gabapentin and between 20 and 100 ppm of an anion of a mineral acid with respect to the weight of gabapentin, and which, after one year of storage at 25° C. and 50% humidity the conversion of gabapentin to the corresponding lactam does not exceed 0.2% by weight of gabapentin.

7. A pharmaceutical composition comprising gabapentin and at least one adjuvant, and initially containing less than 0.5% by weight of a corresponding lactam with respect to the weight of gabapentin and having greater than 20 ppm of chloride with respect to the weight of gabapentin, which, after one year of storage at 25° C. and 50% humidity the conversion of gabapentin to the corresponding lactam does not exceed 0.2% by weight of gabapentin.

* * * * *

UNITED STATES PATENT AND TRADEMARK OFFICE
CERTIFICATE OF CORRECTION

PATENT NO. : 6,531,509 B2
DATED : March 11, 2003
INVENTOR(S) : Singer et al.

It is certified that error appears in the above-identified patent and that said Letters Patent is hereby corrected as shown below:

Column 7,
Line 26, change "250°C" to -- 25°C --

Column 8,
Line 63, change "72" to -- 7.2 --
Line 67, change "examples" to -- examples. --

Column 11,
Line 31, change "tables" to -- tablets --

Column 12,
Line 30, change "gels" to -- gels, --
Lines 45 and 53, change "50%" to -- 60% --

Signed and Sealed this

Twenty-fourth Day of June, 2003

JAMES E. ROGAN
*Director of the United States Patent and Trademark Office*